United States Patent [19]

Songstad et al.

[11] Patent Number: 5,717,129
[45] Date of Patent: Feb. 10, 1998

[54] METHODS FOR MAINTAINING STERILITY IN PLANTS

[75] Inventors: David D. Songstad; Steven J. Corak; Dorothy A. Pierce; Marc Albertsen, all of Polk County, Iowa

[73] Assignee: Pioneer Hi-Bred International, Inc., Des Moines, Iowa

[21] Appl. No.: 389,389

[22] Filed: Feb. 16, 1995

[51] Int. Cl.$^6$ .................... A01H 1/06; A01H 4/00; C12N 15/00; C12N 15/63

[52] U.S. Cl. .................... 800/205; 47/58; 47/DIG. 1; 435/172.1; 435/172.3; 935/35; 935/30

[58] Field of Search .................... 800/205; 47/58, 47/DIG. 1; 435/172.3, 172.1; 935/30, 35

[56] References Cited

U.S. PATENT DOCUMENTS

| | | | |
|---|---|---|---|
| 2,967,376 | 1/1961 | Scott . | |
| 3,710,511 | 1/1973 | Patterson | 47/58 |
| 3,911,183 | 10/1975 | Hinkes | 428/15 |
| 4,068,602 | 1/1978 | Mickus et al. | 111/1 |
| 4,372,080 | 2/1983 | Rushing et al. | 47/57.6 |
| 4,438,593 | 3/1984 | McNew et al. | 47/57.6 |
| 4,517,763 | 5/1985 | Beversdorf | 47/58 |
| 4,727,219 | 2/1988 | Brar et al. | 800/235 |
| 4,734,120 | 3/1988 | Kehne et al. | 71/87 |
| 4,735,017 | 4/1988 | Gago et al. | 47/57.6 |
| 4,761,423 | 8/1988 | Szegö et al. | 514/395 |
| 4,879,839 | 11/1989 | Gago et al. | 47/57.6 |
| 4,975,374 | 12/1990 | Goodman et al. | 435/172.3 |
| 5,071,464 | 12/1991 | Bauer et al. | 71/86 |
| 5,077,399 | 12/1991 | Brauer et al. | 536/27 |
| 5,098,838 | 3/1992 | Goodman et al. | 435/183 |
| 5,106,649 | 4/1992 | Spicer et al. | 427/4 |
| 5,145,777 | 9/1992 | Goodman et al. | 435/172.3 |
| 5,173,103 | 12/1992 | Yoshida et al. | 71/86 |
| 5,364,780 | 11/1994 | Hershey et al. | 47/1 |
| 5,369,022 | 11/1994 | Newhouse et al. | 435/172.3 |
| 5,420,034 | 5/1995 | Kridl et al. | 435/240.4 |

FOREIGN PATENT DOCUMENTS

| | | | |
|---|---|---|---|
| 1251653 | 3/1989 | Canada . | |
| 0198288 | 10/1986 | European Pat. Off. | C12N 15/00 |
| 0344029 | 11/1989 | European Pat. Off. | C12N 5/00 |
| 0375875 | 7/1990 | European Pat. Off. | C12N 15/52 |
| WO 90/08830 | 8/1990 | European Pat. Off. | 435/172.3 |
| 0412911 | 2/1991 | European Pat. Off. | C12N 15/82 |
| 2208346 | 3/1989 | United Kingdom | A01H 1/02 |
| WO 93/25695 | 12/1993 | WIPO | C12N 15/82 |

OTHER PUBLICATIONS

Szell E. Acta Phytopathologica et Entomologica Hungarica 28 (2–4) Biosis 95:478491, 1993.
Schena et al. PNAS Vo. 88 pp. 10421–10425, 1991.
Yamaguchi–Shinozaki et al. Pl. Mol. Bio. vol. 15:pp. 905–912, 1990
Mariani et al. Nature vol. 357 pp. 394–387, Jun. 4, 1992.
"Cultivation of Rice Using Seeds Coated with Algicides and Herbicides", Chemical Abstracts, vol. 107, No. 15, p. 264, Oct. 1987.

(List continued on next page.)

Primary Examiner—Gary Benzion
Attorney, Agent, or Firm—Pioneer Hi-Bred International, Inc.

[57] ABSTRACT

A method of maintaining sterility in plants is disclosed. The method comprises genetic transformation of parental plant lines with a sterility gene that is genetically linked to a resistance gene which confers resistance to a selective agent, increasing the transgenic parental line and coating the seed of the increased transgenic parental line with a composition comprising the selective agent to which the resistance gene confers resistance. The resistance gene can be under the control of an inducible gene, or, alternatively, under the control of constitutive or tissue specific, including seed-specific, promoters.

29 Claims, 1 Drawing Sheet

OTHER PUBLICATIONS

Bidney et al. (1992) Microprojectile Bombardment of Plant Tissues Increases Transformation Frequency by *Agrobacterium tumefaciens, Plant Molecular Biology,* 18:31–313.

Bowen, Benjamin A. (1993) Markers for Plant Gene Transfer, *Transgenic Plants,* vol. 1, pp. 89–123.

Davis, et al. (1991) Chemical Regulation of Vegetative Growth*, *Critical Reviews in Plant Sciences,* 10(2):151–188.

Everett, et al. (1987) Genetic Engineering of Sunflower (*Helianthus annuus L.*), *Bio/Technology,* vol. 5, pp. 1201–1204.

Glick, et al. (1993), Methods in Plant Molecular Biology and Biotechnology,*Vectors for Plant Transformation,* pp. 89–119.

Goddijin et al.(1993) A chimaeric tryptophan decarboxylase gene as a novel selectable marker in plant cells, *Plant Molecular Biology,* 22:907–912.

Gunsolus, Jeff (1993) Chart Your Chemical's Family Tree, *Soybean and Digest,* p. 17.

Hedberg et al. (1993) Herbicide–Tolerant–Crops–Impacts on the North American Seeds and Crop Protection Chemicals Industries, *The Bowditch Group, Inc.,* pp. 1–95.

Holt et al. (1993) Mechanisms and Agronomic Aspects of Herbicide Resistance, *Annul. Rev. Plant Physiol. Plant Mol. Biol.,* 44:203–29.

Weide et al. (1989) A simple, nondestructive spraying assay for the detection of an active kanamycin resistance gene in transgenic tomato plants, *Theot. App. Genet.,* 78:169–172.

Wilmink et al. (1993) Selective agents and markers for transformation of monocots, *Plant Molecular Biology Reporter,* vol. 11(2).

Wintersteen et al. (1993) Seed Treatment, *Iowa Commercial Pesticide Applicator Manual,* p. 16.

METHODS FOR MAINTAINING STERILITY IN PLANTS

FIELD OF THE INVENTION

The present invention relates to a method for maintaining sterility genes in plants, and to the plants produced using the method.

BACKGROUND

The goal of plant breeding is to combine in a single variety or hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

In Brassica, the plant is normally self sterile and can only be cross-pollinated. In self-pollinating species, such as soybeans and cotton, the male and female organs are anatomically juxtaposed. During natural pollination, the male reproductive organs of a given flower pollinate the female reproductive organs of the same flower.

Maize plants (*Zea mays L.*) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

A reliable method of controlling fertility in plants would offer the opportunity for improved plant breeding and hybrid production. In particular, control of male fertility is significant in relation to commercial production of hybrids. This is especially true for development of crop species sold solely as hybrids, for example sorghum and maize, both of which have historically relied upon some sort of male sterility system. In addition, such a method would be useful in crops such as soybeans, sunflower, canola, wheat, and others which have in the past not been amenable to hybridization.

The production of maize hybrids requires the development of essentially homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield. These manifestations of heterosis are particularly significant from a commercial standpoint; increased yield is particularly important, both to seed corn companies and to farmers, and high-yielding hybrid corn lines have become the commercial products of choice in the seed corn industry.

Hybrid maize seed is typically produced by a male sterility system incorporating manual detasseling. Alternate strips of two inbred varieties of maize are planted in a field, and the pollen-bearing tassels are removed from one of the inbreds (female). With sufficient isolation from sources of foreign maize pollen, the ears of the detasseled inbred will be fertilized only with pollen from the other (male) inbred, and the resulting seed is therefore hybrid and will form hybrid plants.

Unfortunately, although the manual detasseling process is very reliable, it is also a very labor-intensive process which must be carried out within a specific, critical time window, and if there is a shortage or unavailability of labor, the critical window for detasseling can be missed. In addition, a female plant will occasionally be blown over by a storm and will escape detasseling. Additionally, environmental factors can cause plants to produce secondary tassels after manual detasseling is completed. Or, a detasseler will not completely remove the tassel of the plant, or tillers may form on female plants, or tassels may shed while still in the whorl. In any event, such female plants will successfully shed pollen and some female plants will be self-pollinated. This will result in seed of the female inbred being harvested along with the hybrid seed which is intended to be produced. This is a significant disadvantage, because inbred lines are not generally intended for commercial sale, in that they do not have the commercial yield of hybrids, and inbreds are typically not made publically available unless they are legally protected.

Alternatively, the female inbred can be mechanically detasseled. Mechanical detasseling is approximately as reliable as manual detasseling, but is faster and less costly. However, most detasseling machines produce more damage to the plants than manual detasseling, and final clean-up after mechanical detasseling always requires manual detasseling in any event. Thus, no form of detasseling is presently entirely satisfactory, and a need continues to exist for alternatives which further reduce production costs and eliminate self-pollination in the production of hybrid seed.

The laborious detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown.

There can be other drawbacks to CMS. One is an historically observed association of a specific variant of CMS with susceptibility to certain crop diseases. This problem has led to virtual abandonment of use of that particular CMS variant in producing hybrid maize, although other CMS systems are still in use.

Another form of sterility, a type of genetic male sterility, known as nuclear male sterility, is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make the use of the system convenient. Patterson also described a nuclear male sterility system incorporating chromosomal translocations which are effective, but complicated. See U.S. Pat. No. 3,861,709 and 3,710,511.

Many other attempts have been made to improve on these drawbacks. For example, Fabijanski, et al., developed several methods of causing male sterility in plants (see EPO 89/3010153.8, publication no. 329,308, and PCT application PCT/CA90/00037, published as WO 90/08828). One method includes delivering into the plant a gene encoding a cytotoxic substance associated with a promoter specific for male tissue. Another involves an antisense system in which a gene critical to fertility is identified and a gene which is antisense to the fertility gene is inserted in the plant. Mariani, et al. also shows several cytotoxin encoding gene sequences, along with male tissue specific promoters and mentions an antisense system. See EP 89/401,194. Still other systems use "repressor" genes which inhibit the expression of another gene critical to male fertility. PCT/GB90/00102, published as WO 90/08829.

Other aspects of the work underway with male sterility systems relate to the identification of genes impacting male fertility. Such a gene can be used in a variety of systems to control male fertility. Previously, a male fertility gene has been identified in *Arabidopis thaliana* by transposon-induced male sterile mutants, and the gene was then cloned. Aarts, et al., "Transposon Tagging of a Male Sterility Gene in Arabidopsis", *Nature*, 363: 715–717 (Jun. 24, 1993). Another important male fertility gene is disclosed in pending U.S. patent application Ser. No. 08/013,739, which is a continuation-in-part of pending U.S. patent application Ser. No. 07/537,183. See also Albertsen et al., Am. J. Botany 80: 16 (1983).

Regardless of the system used to achieve male sterility, as noted above male sterility is of critical importance in the production of commercial hybrids. The presence of non-sterilized males in a commercial production field can have disastrous consequences since undirected crosses and/or self-pollinated seed will result, and consequently "contaminants" (in this context, seed having a genetic make-up other than that of the hybrid which is intended to be produced) will be present.

Once transgenic male sterile parental lines have been produced, it becomes crucial to develop a strategy for maintaining male sterility genes, and to eliminate male fertiles, in progeny of maize inbreds. This is essential for utilization in commercial seed production. For example, one strategy would be to link the male sterility gene with the Bar herbicide resistance gene, and maintain this trait as a heterozygote by outcrossing. Outcrossed progeny from this should segregate 1 sterile: 1 fertile. In this manner, the fertile plants can be eliminated by spray application of an appropriate herbicide: Basta™, for example.

Several limitations are associated with this approach. Spraying herbicides is in itself a potentially dangerous practice, and the cost of the specialized equipment required for spraying is often prohibitive. Also, some herbicides can have particularly devastating effects on the health of surviving plants, and may in some cases have potential long-range effects. For example, glyphosate is known to be translocated and stored in meristematic tissue, and this can negatively affect fertility. Moreover, a significant limitation of this approach is herbicide drift, which kills the non-transgenic male parent in hybrid seed production. However, one will recognize that these are more spraying or application problems, or whole-plant treatment problems, than herbicide problems per se. An alternative method for herbicide application that avoids drift should alleviate this problem.

Coating of seed for protection against fungi and for maintenance of mechanical integrity has been described in U.S. Pat. No. 4,438,593 issued to McNew, et al. Coating of seed with Captan™ or phosphinothricin derivatives using adhesive agents has also been disclosed in the McNew, et al. patent, as well as U.S. Pat. No. 5,145,777 (Goodman, et al.) and Canadian Patent No. 1,251,653A. Genetic transformation of plants to produce herbicide resistance is well known in crop science (see, for example, U.S. Pat. No. 4,975,374). Furthermore, U.S. Pat. No. 5,369,022 discloses a method to improve the protection of crops from herbicidal injury by incorporating genetically imparted resistance to the herbicide in combination with treating seed of the crop with an antidotal amount of a chemical safener to the herbicide. However, the novel combination of seed coating, genetically induced resistance, and genetic transformation, to maintain sterile plants provides a unique method of maintaining sterility genes in progeny which addresses many of the problems outlined above.

SUMMARY

The present invention provides a method for maintaining sterility in plants. The method involves the generation of a transgenic parental plant line which comprises a sterility gene genetically linked to a gene which confers resistance to a selective agent, for example a herbicide, an antibiotic, a substrate such as 4-methyltryptohan (4-mT), or the like. The transgenic parental plant line is increased by traditional plant breeding methods, and seed of the increased transgenic parental plant lines are coated with a composition comprising the selective agent to which the resistance gene confers resistance. The sterility genes useful in the practice of the invention include, for example, the pAN::Tox gene, the dam methylase gene, the ACC synthase gene, and the like.

The invention envisions that the sterility gene is genetically linked to a gene which confers resistance to a selective agent, for example a herbicide, or an antibiotic, or some other suitable agent, for example a toxic substrate, such as 4-mT. The resistance gene may be under the control of a constitutive promoter, or alternatively may be under the control of a seed specific promoter, or alternatively may be under the control of an inducible gene, for example one induced by a hormone, or by another non-hormone chemical substance, for example a non-hormone protein, or a chemical "safener", or some other form of chemical ligand. According to this embodiment of the method of the invention, seeds of the parental line are coated with a mixture comprising an effective amount of both the selective agent to which resistance has been conferred genetically, as well as the chemical which induces resistance. In a further alternative embodiment the resistance gene may be under the control of a seed-specific promoter. A particular advantage of these embodiments relates to the fact that expression of the resistance gene can be limited to the seed stages of development. These embodiments therefore have particular advantages in limiting or restricting the expression of genes which are subject to governmental regulatory oversight. Specifically, these embodiments of the invention, particularly the embodiment relating to the use of a seed-specific promoter, have the advantage of restricting expression of the resistance gene to the seed and avoiding the potential regulatory issues associated with resistance in crops such as sunflower, sorghum and canola, crops in which resistance could be outcrossed into wild species. These embodiments provide the further advantage of avoiding the need to market seed which will give rise to plants which could putatively express resistance genes in the whole plant throughout the plants' lifetimes.

An objective of the method of the invention is to provide a system whereby application of a selective agent, a herbicide for example, to the seed of plants would result in wild-type plant death and survival of resistance plants, so that spraying or other forms of general, whole plant, environmental application is avoided, and so that wild-type male fertile plant death and survival of resistant plants could be accomplished at early, and in certain embodiments selected, stages of development.

A general advantage of the method of the invention is the avoidance of the need to apply potentially hazardous chemicals onto plants in the field, thereby decreasing the amount of such chemicals used in and introduced into the environment. An additional advantage of the invention is that the method will foster development of hybrids in self-pollinating species, such as soybeans, and in species which have not been amenable to manual detasseling, such as sorghum.

In addition, the present invention further envisions planting coated transgenic seed, growing up therefrom mature, transgenic, male sterile plants, fertilizing the mature male sterile plants, and harvesting the fertilized seed of those plants. The present invention further relates to the seed produced according to the method of the invention.

DETAILED DESCRIPTION

Figure 1:
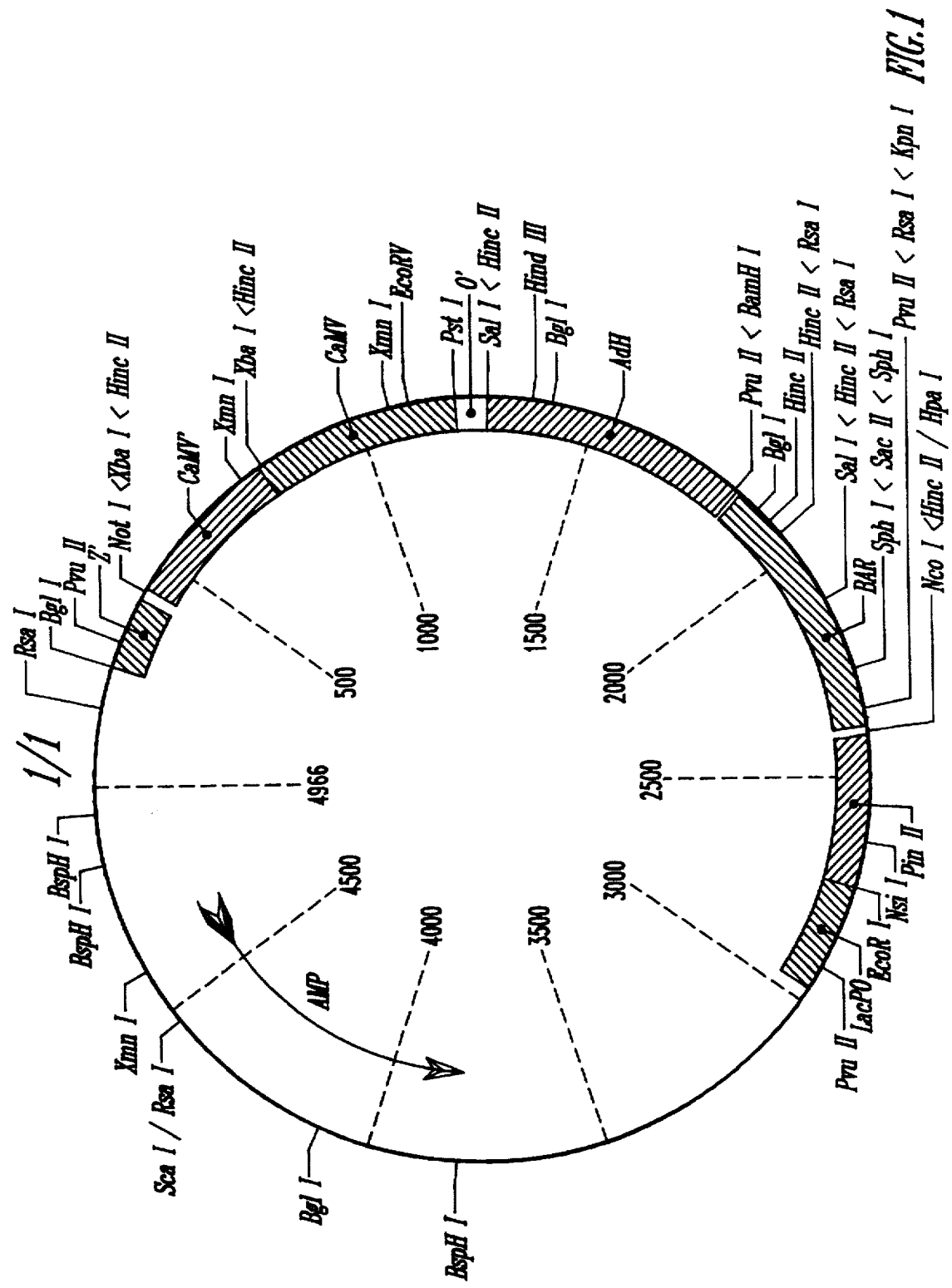
FIG. 1 is a plasmid map of the pPHP610 plasmid.

Transgenic parental plant lines can be generated using a number of methods recognized in the art, including, for example, microprojectile bombardment, is microinjection, Agrobacterium-mediated methods, electroporation, and the like. See generally, Glick and Thompson, *Methods in Plant Molecular Biology and Biotechnology*, CRC Press, 1993. As those skilled in the art will recognize, choice of transformation method and conditions will vary depending upon the plant species being subjected to the method of the invention.

Any gene construct which confers sterility can be applied in the method of the invention. For example, in a preferred embodiment of the method of the invention the construct conferring sterility is the pAN::tox construct. Other genes useful in conferring sterility have been described in the art (see the references cited above), and include, for example, dam methylase and ACC synthase. As used herein, "sterility gene" refers to a gene which actively promotes or confers sterility, and may include heterologous genes such as the Barnase gene, the dam methylase gene, and the like, or may constitute a gene which is antisense to a fertility gene.

The present invention also involves the use of a resistance gene which confers resistance to a selective agent genetically linked to the sterility gene. "Genetically linked" is used herein to refer to an association, either direct or indirect, between the two genes such that during transformation they are delivered into the plant cells in the same transformation event, and are incorporated into the genetic material of the recipient plant in such a manner that during parent seed increase the genes maintain their functional association.

The method of the invention relates to genetically linking the sterility gene to a resistance gene, for example a gene for herbicide resistance, or for antibiotic resistance, or genes which alter metabolism so as to allow for metabolism of toxins or other selective substrates. The resistance gene confers resistance to a corresponding selective agent: herbicide resistance genes to herbicides; antibiotic resistance genes to antibiotics, and other chemical resistance genes to their respective chemical agents, for example the gene for tryptophan decarboxylase, which confers resistance to 4-mT.

In one embodiment of the method of the invention, the sterility gene is genetically linked to a gene which confers herbicide resistance. Resistance may be conferred to herbicides from several groups, including amino acid synthesis inhibitors, photosynthesis inhibitors, lipid inhibitors, growth regulators, cell membrane disrupters, pigment inhibitors, seedling growth inhibitors, and the like, and examples of specific herbicides applicable to the method of the invention include: imidazolinones, sulfonylureas, triazolopyrimidines, glyphosate, sethoxydim, fenoxaprop, glufosinate (for example bialaphos), the triazines, bromoxynil, and the like. See, for example, Holt, J. S., *Mechanisms and Agronomic Aspects of Herbicide Resistance*, Ann. Rev. Plant Physiol. Plant Mol. Biol. 44: 203–29, 1993; Wilmink et al., *Selective Agents and Marker Genes for Transformation of Monocotyledonous Plants*, Plant Mol. Biol. Sep. 11, 1993; Gunsolus, *Chart Your Chemical's Family Tree*, Soybean Digest, April, 1993. In a specific embodiment of the present invention, the commercial herbicide Basta™ is used. Genes appropriate for use in this embodiment of the method of the invention include, for example, Bar, PAT, aroA, Epsps, cor1-1, bxn, and psbA.

In an alternative embodiment of the present invention, the sterility gene is genetically linked to a gene which confers antibiotic resistance. Antibiotics useful in the practice of the invention include, for example, the aminoglycoside antibiotics, for example kanamycin, genetamycin, G418, neomycin, paromysin, and hygromycin, and the genes useful in the practice of this embodiment of the invention include, for example, NPT II, the aphA2 gene from Tn5 of *E. coli*, and the pht-aphlV gene from *E coli*. See Wilmink et al., op. cit. See also, Bowen, B. A., *Markers for Plant Gene Transfer*, Transgenic Plants, Vol. 1, Engineering and Utilization, 1993; Everett et al., *Genetic Engineering of Sunflower (Helianthus annus L.)*. Bio/Technology 5: 1201–1204 (1987); Bidney et al., Plant Mol. Biol. 18: 301–313 (1992).

In a further alternative embodiment of the invention, the sterility gene is linked to a resistance gene which confers resistance to a particular chemical, for example one which is toxic to the plant. One example would be the gene for tryptophan decarboxylase, which confers resistance to 4-mT. See Goodijn et al., *A Chimeric Tryptophan Decarboxylase Gene as a Novel Selectable Marker in Plant Cells*, Plant Mol. Biol, 22: 907–912, 1993. See also Bowen, op. cit.

In one embodiment of the invention, the resistance gene is under the control of a constitutive promoter. In an alternative embodiment of the invention, the resistance gene is under the control of a promoter induced by a particular chemical (an inducible promoter). For example, the resistance gene may be induced by a hormone, for example, a protein hormone or asteroid hormone, or by a chemical "safener". Examples of steroid hormones effective in the practice of the invention would be the estrogens, the glucocorticids, and the like. See, e.g., Gronemeyer, *Transcription Activation by Estrogen and Progesterone Receptors*, Ann. Rev. Genet. 35: 89–123, 1991. See also, Glick and Thompson (cited above), in particular Graber and Crosby, *Vectors for Plant Transformation*, at pp. 89–119, for a discussion of inducible promoters. For a discussion of other chemical agents, see Hershey and Stoner, *Isolation and Characterization of a cDNA Clones for RNA Species Induced by Substituted Benzene-Sulfonamides in Corn*. Plant Mol. Biol. 17: 679–690. See also U.S. Pat. No. 5,364,780 for a discussion of "safeners". In these latter alternative embodiments, it will be obvious to one skilled in the art that the seeds would be coated with mixtures comprising the specific chemical to which the inducible gene responds, along with the particular selective agent. Alternatively, tissue specific, or more particularly seed-specific expression, could be genetically provided. Glick and Thompson, op. cit.

Once suitable transgenic parental lines have been produced, the method of the present invention involves the increase of the parental lines, using methods well known in the plant breeding arts. Once the parental lines have been increased sufficiently, seed of the increased line can be collected by means familiar to, and recognized by, those skilled in the plant breeding ads.

Seed collected from increased transgenic parental lines can be coated in any convenient manner. For example, in one specific embodiment of the invention an equal volume of a 10% active ingredient working solution of Captan™ (N-trichloromethylthio-4-cyclohexene-1, 2-dicarboximide [active ingredient], dipropylene glycol [adhesive], and polyox (WSRN10) [adhesive] (final concentrations being 42.5% Captan™, 54.5% dipropylene glycol, and 3% polyox) is mixed with a commercial formulation of Basta™ (20% phosphinothricin [DL-homoalanine-4-yl-(methyl)-phosphinic acid; see Droge et al., Planta 187: 142–151, 1992], active ingredient) at a ratio of 1:1 (vol—vol). The mixture can be applied to the seeds in any convenient manner. Coating may proceed in either a sequential (Captan™ followed by selective agent and, if applicable, inducer) or a simultaneous treatment, although sequential treatment steps are presently preferred. Alternative formulations will be readily apparent to those skilled in the art; for example a 1:1 (vol:vol) mixture of Captan™ working solution and methionine sulfoximine (MSO) can be used. Alternative formulations of various binders and alternative selective agents can be routinely screened for efficacy by screening for germination of seeds coated with coating mixtures containing increasing concentrations of binder and/or selective agent, and similar screening processes can be conveniently performed for coatings containing additional alternative chemical ligands for practice of the invention using an inducible system.

After the coated seeds have dried they are planted as appropriate to plant type, and resistant sterile seed will germinate and grow. Hybrid plant production can then proceed according to methods well known in the plant breeding arts.

The following examples are intended to illustrate the invention but not to limit its scope.

EXAMPLE 1

Effect of Seed Coating on Seedling Survival

The present example sets forth the results of experiments performed to determine the effect of seed coating on seedling survival in wild-type and transgenic seed.

Materials and Methods

Seed was obtained from a variety of transgenic TO and wild-type Hi-II plants. Unless otherwise mentioned, kernels were chipped for PCR analysis to indicate which of the selfed TO progeny did/did not contain the Bar gene. Kernels were then immersed in a 1:1 mixture of Captan™ (standard 10% active ingredient working solution used in seed production) and Basta™ commercial formulation (20% active ingredient). Similar kernel coating was performed using a 1:1 mixture of Captan™ and methionine sulfoximine (20% aqueous solution). Seed was then allowed to air dry to a pink color characteristic of Captan™. Bar positive kernels were planted in a separate greenhouse pot from those that were Bar negative. In a subsequent experiment, kernels were not chipped for PCR but coated with Basta™-Captan™, planted in greenhouse pots and leaf material collected from surviving plants for PCR analysis.

Wild type maize kernels were either coated with Basta™-Captan™ or left untreated and planted in separate pots. Out of 13 kernels, all of the untreated ones germinated and produced seedlings. However, none of the Basta™-treated kernels were able to germinate and develop into seedlings. These results suggested that application of Basta™ to the seed surface was a successful method of applying a lethal dose of this herbicide.

This method of herbicide application was then repeated with transgenic seed. Prior to Basta™ or MSO treatment, transgenic T1 kernels were PCR chipped to determine which ones were Bar negative and Bar positive. Results from the second seed coating experiment are listed in Table 1. No kernels that were Bar negative survived to form a seedling whereas 80% and 53% of those Bar positive kernels coated with Basta™ or MSO, respectively, developed into plants. The Bar negative kernels were viable and germinated to form roots but failed to form shoots. The same was apparent with the Bar negative kernels treated with MSO.

The advantages of coating Basta™ or MSO onto kernels are as follows: First, it is a rapid method whereby thousands of kernels can be treated in a matter of minutes. Second, this technology fits perfectly with the current use of Captan™ as a seed treatment. Third, it alleviates the problems associated with spraying, such as the need for expensive equipment, herbicide drift, and others as mentioned above. Fourth, it is an elegant and novel solution to a significant problem.

As seen in Table 1, only about half of the Bar positive kernels were capable of surviving the MSO treatment as compared to 85% of those treated with Basta™. The exact reason for this is still not resolved; without intending to be limited by theory, it may be that too much MSO was applied to the surface of the kernels and that lower levels would result in better survival of Bar positive transformed progeny.

TABLE 1

EFFECT OF BASTA AND MSO SEED COATING ON SEEDLING SURVIVAL 10 DAYS AFTER PLANTING IN GREENHOUSE

| Chemical | Bar Negative | Bar Positive |
|---|---|---|
| Basta | 0/15* | 12/15 |
| MSO | 0/15 | 8/15 |

*Numerator refers to number of surviving seedlings. Denominator refers to number of seeds that were planted.

EXAMPLE 2

Herbicide Coating Growth Chamber Test and Field Trial

A preliminary experiment was conducted in the growth chamber to test for the expression of the herbicide-resistance trait in four separate pedigree backgrounds. The second portion of this study was a field trait that was conducted at two locations (Dysart, Iowa and Johnston, Iowa) during the 1994 growing season. The field trial was covered under the USDA Environmental Release Permit #94-056-05N.

Materials and Methods

1) Preliminary Growth Chamber Test

Treatments for this preliminary test were a factorial combination of four genotypes and three rates of herbicide coating. Seed were obtained from two transgenic (35S::BAR) T1 populations by crossing with various elite female inbred parents: Inbred Lines A, B, C, and D. On May 6, individual batches (30 seed per batch) were treated with 0.08 ml of Captan™. Immediately after applying the Captan™, each batch was treated with either 0, 0.12, or 0.60 ml ("zero", "low", and "high") of a solution the glufosinate-containing herbicide known as Basta™ (Hoechst) at a concentration of 20% active ingredient. A rotary treater manufactured by Hans-Ulrich Hege ("HEGE 11") was used to apply the Captan™ and Basta™ treatments.

Each of three plastic boxes were filled with 2 kg of the air-dried soil. On May 6, three rows (15 kernels per row) of a single genotype were planted in each box. Rows represented either the zero, low, or high rate of Basta™. The dry soil was covered with paper towels and then 500 ml of tap water were poured over the towels. The towels were removed once the water had soaked into the soil. Boxes were sealed with lids and then placed in a dark, temperature-controlled chamber set at 22° C. On May 17, emergence counts were recorded. Etiolated seedlings were classified as either normal or abnormal based upon appearance relative to the untreated controls. Tissue from emerged seedlings was harvested and used to generate Southern profile data (See Example 3 below).

II. Field Trial

Treatments for the experiment were a factorial combination of four genotypes and six rates of herbicide coating. Each genotype was a whole-plot, and a single row (17.5-ft long) of each herbicide-coating rate was a subplot. The entire experiment was arranged as a randomized complete block design with three replications at each location. Seeds were obtained from two transgenic (35S::BAR) T1 populations by crossing with the elite female inbred parents of Example 1: Inbred Lines A, B, C and D. On May 18, small batches (325 seed per batch) were treated with 0.86 ml of Captan™ slurry. The following day, individual batches of seed were treated with either 0, 1.30, 2.60, 3.90, 5.20, or 6.50 ml of Basta. The HEGE 11 was used to apply the Captan™ and Basta™ treatments. One day after application of Basta™, all seed were coated with talcum powder to prevent the kernels from sticking together during planting.

Conventional tillage was used to prepare a fine seedbed at each location. Dual herbicide was incorporated for pre-plant seed control at Dysart. Seeds were planted by hand (28 kernels were per row) at a depth of 2 to 5 cm using a traditional push planter. Planting dates were May 27 for Johnston and June 1 for Dysart. Pounce™ was applied for control of cutworms on June 3 at Johnston. Weeds emerging during the experiment were removed by hand hoeing.

Emergence data were recorded for each subplot on June 7 at Johnston and June 17 at Dysart. During June 21 to 24 at Johnston, and June 27 to 28 at Dysart, each plant in the experiment was assigned an identification number that was recorded on a small plastic stake placed in the ground immediately adjacent to the plant. At the same time, a small leaf punch was removed from an upper leaf of the plant and then placed in a labeled plastic vial. The label on the vial corresponded to the identification number of the plant in the field. Leaf punches were stored in a freezer for future PCR analysis.

On July 6, all plots at both locations were sprayed with Basta™ using a $CO_2$-charged backpack sprayer. The application rate of Basta™ was 6.4 pints per acre with a carrier volume 30 gallons of water per acre. Three nozzles directed the herbicide to the top and both sides of the plants. Coverage was excellent, and the weather conditions were warm and dry.

The identification numbers of those plants that were sensitive to Basta™ were recorded on July 11 at Johnston and July 12 at Dysart. Sensitivity to Basta™ was obvious; the plants were yellow and had areas of necrotic tissue. Resistant plants appeared normal, except for a limited degree of speckling on some leaves. Without intending to be limited by theory, this effect was most likely caused by a non-active ingredient in the herbicide, and was markedly less severe than the general decline observed in the sensitive plants.. Immediately following data collection, all plants were chopped at the soil surface and then the residues were disked into the soil. Plots were monitored to insure that no plants were able to recover or shed pollen.

Results and Discussion

In the preliminary growth chamber study, emergence was nearly 100% for the kernels that were not coated with Basta™; these seedlings appeared normal (Table 2). Application of Basta™ reduced the rate of emergence. At the low rate of Basta™, some of the emerged seedlings were very delayed and appeared abnormal relative to the controls. We postulated that these abnormal plants were non-transformed segregants that were showing herbicide injury. Fewer abnormal seedlings occurred at the high rate, undoubtedly because the non-transformed segregants were successfully killed by the herbicide. In retrospect, this test should have been conducted in the light rather than the dark because the herbicide should show greater phytotoxicity in the light.

To briefly summarize the results of the field trial, we observed that treatment of kernels with Basta™ completely eliminated the emergence of Basta™-sensitive plants (Table 3). Control of the Basta™-sensitive segregants was obtained at even the lowest rate of Basta™ applied to the kernels. This conclusion is based upon the fact that the only plants that showed susceptibility to the foliar-applied herbicide were in the control plots that did not have Basta™ on the kernels (Table 4). The percent stand reduction that resulted from treating the kernels was consistent with the expected segregation ratio for the herbicide-resistance trait. Based upon the clear-cut results, it was decided that it would not be necessary to do any PCR analysis on the leaf disks that were collected during the experiment.

TABLE 2

Results of Preliminary Growth Chamber Test - Seedling Emergence as Affected by Basta ™ Kernel Coating

| | Basta Rate | | |
|---|---|---|---|
| Genotype (by female) | Zero | Low #Emerged | High |
| Inbred A | 15 (all normal) | 5 (normal) 8 (abnormal) | 7 (normal) 4 (abnormal) |
| Inbred B | 14 (all normal) | 4 (normal) 1 (abnormal) | 7 (normal) 1 (abnormal) |

TABLE 2-continued

Results of Preliminary Growth Chamber Test - Seedling Emergence as Affected by Basta ™ Kernel Coating

| Genotype (by female) | Basta Rate | | |
|---|---|---|---|
| | Zero | Low #Emerged | High |
| Inbred C | 15 (all normal) | 8 (normal) 2 (abnormal) | 8 (all normal) |
| Inbred D | 15 (all normal) | 5 (normal) 5 (abnormal | 7 (all normal) |

TABLE 3

Percentage Plant Emergence From Seed Coated with Basta ™ and Captan ™

| Location | Female inbred | Basta ™ Dose Rate | | | | | |
|---|---|---|---|---|---|---|---|
| | | 0X | 1X | 2X | 3X | 4X | 5X |
| Johnston | A | 90.5 ± 10.9* | ND | 46.4 ± 12.4 | 33.3 ± 4.1 | 35.7 ± 12.9 | 41.7 ± 14.4 |
| | B | 97.6 ± 2.1 | 35.7 ± 4.1 | 31.0 ± 4.1 | 31.0 ± 2.1 | 36.1 ± 4.1 | 31.0 ± 7.4 |
| | C | 92.9 ± 6.2 | 35.7 ± 12.9 | 47.6 ± 16.1 | 51.2 ± 8.2 | 42.9 ± 15.6 | 38.1 ± 11.5 |
| | D | 92.9 ± 6.2 | 40.5 ± 12.5 | 54.8 ± 11.5 | 47.6 ± 4.1 | 51.2 ± 8.2 | 47.6 ± 11.5 |
| Dysart | A | 92.9 ± 6.2 | ND | 39.3 ± 3.6 | 32.1 ± 6.2 | 38.1 ± 5.5 | 39.3 ± 9.4 |
| | B | 96.4 ± 0.0 | 27.4 ± 7.4 | 42.9 ± 3.6 | 32.1 ± 6.2 | 35.7 ± 17.9 | 33.3 ± 5.5 |
| | C | 90.5 ± 7.4 | 51.2 ± 2.1 | 39.3 ± 7.1 | 54.8 ± 13.5 | 46.4 ± 7.1 | 41.7 ± 14.9 |
| | D | 95.2 ± 2.1 | 42.9 ± 12.9 | 61.9 ± 10.9 | 48.8 ± 11.5 | 54.8 ± 20.6 | 45.2 ± 5.5 |

*Values represent means from three replications ± S.D.

TABLE 4

Percentage of Plants That Were Sensitive to a Foliar Application of Basta ™

| Location | Female Inbred | Basta ™ Dose Rate | | | | | |
|---|---|---|---|---|---|---|---|
| | | 0X | 1X | 2X | 3X | 4X | 5X |
| Johnston | A | 50.0 ± 9.4* | 0.0 | 0.0 | 0.0 | 0.0 | 0.0 |
| | B | 58.3 ± 13.5 | 0.0 | 0.0 | 0.0 | 0.0 | 0.0 |
| | C | 44.0 ± 5.5 | 0.0 | 0.0 | 0.0 | 0.0 | 0.0 |
| | D | 42.9 ± 9.4 | 0.0 | 0.0 | 0.0 | 0.0 | 0.0 |
| Dysart | A | 48.8 ± 9.0 | 0.0 | 0.0 | 0.0 | 0.0 | 0.0 |
| | B | 69.0 ± 7.4 | 0.0 | 0.0 | 0.0 | 0.0 | 0.0 |
| | C | 53.6 ± 9.4 | 0.0 | 0.0 | 0.0 | 0.0 | 0.0 |
| | D | 52.4 ± 4.1 | 0.0 | 0.0 | 0.0 | 0.0 | 0.0 |

*Values represent means from three replications ± S.D.

EXAMPLE 3

Southern Analysis of Growth Chamber Grow-Out

Four populations of maize were transformed by microparticle bombardment, with plasmid pPHP610 (Pioneer Hi-Bred International, Inc.) containing the Bar gene. Seed was coated with Captan™ coating alone (with no added Basta™), or Captan™ plus 0.12 ml Basta™, or Captan™ plus 0.60 ml Basta™. Plants were germinated, and DNA was extracted from surviving plants and was subjected to Southern analysis.

In one form of Southern analysis the putative transformed DNA was digested with a restriction enzyme which was predicted to cut once within the plasmid. This was termed "integration analysis", and for the pPHP610 plasmid EcoR1 was chosen. In an alternative form of Southern analysis, EcoR1/Not1 was chosen in order to provide a digestion wherein the delivered plasmid DNA would be cut twice, and wherein the digestion will drop out a fragment of a known size that will contain as much of the plant transcription unit ("PTU") as possible. "Integration analysis" is designed to theoretically give a different sized hybridizing brand for each different integration site in the plant genome. "PTU" analysis should give a hybridization at a specific fragment size. The presence of different sized hybridization fragments would indicate a complex integration event (e.g., scrambling, deletion, or insertion in the PTU region). Results of Southerns were analyzed for the presence or absence of the Bar gene. The bar coding region was used in all of the analyses, and the template for the probes was a 567 bp Bam H1/Hpa1 fragment from pPHP610. As a negative control, 101 µg of untransformed Hi-II (F2 of B73×A188) DNA was used. As a positive control, plasmid DNA of pPHP610 HI-II equal to 1 copy/genome and 5 copies/ genome were added to 10 µg untransformed Hi-II DNA.

Integration analysis showed single transformation events across elite lines, with somewhat more complex integrations in certain lines. These lines appeared to have three separate integration sites containing three PTUs, one of which appeared to be intact. Only one plant which did not contain the Bar gene germinated from a seed coated with Basta™, and this was not surprising since this plant was from a Basta™ plus Captan™ coated kernel that germinated and developed under sup-optimal conditions (in darkness).

EXAMPLE 4

Ligand Induction of Reporter Gene Via Seed Coating

Seed derived by outcrossing transgenic T0 maize plants containing a suitable hormone-dependent receptor and hormone response element driving the Bar gene with wild type pollen are used as source material. The resulting seed is coated with the following combination of chemicals:

1) Non-coated control
2) Coated with Basta™ only
3) Coated with hormone only
4) Coated with Basta™ and hormone Coated seed is planted in the greenhouse and emergence quantified. Anticipated results would be near 100 percent emergence from the non-coated control seed and from seed coated with hormone only. No emergence would be expected from seed coated with Basta™ only and 50% emergence would be expected from seed coated with Basta™ and hormone.

EXAMPLE 5

Safener Induction of Reporter Gene Via Seed Coating

Seed derived by outcrossing to maize plants containing DNA promoter sequence from IN2-1 or IN2-2 driving the Bar gene with wild type pollen are source material. The resulting heterozygous seed is coated with the following combination of chemicals:

1) Non-coated control
2) Coated with Basta™ only
3) Coated with 2-CBSU safener only
4) Coated with both Basta™ and 2-CBSU Basta™ is applied as described in Example 2, while 2-CBSU is applied at rates of up to the equivalent of 2000 g/ha. Coated seed is planted in the greenhouse and emergence quantified. Anticipated results would be for near 100 percent emergence from the non-coated control seed and from seed coated with 2-CBSU safener only. No emergence would be expected from seed coated with Basta™ alone, while 50% emergence would be expected from seed coated with both Basta™ and 2-CBSU safener.

EXAMPLE 6

Seed-Specific Expression of Resistance

There will be instances in which it will be desirable to use the seed coating system on seed which produce plants that no longer express resistance beyond the seedling stage. For example, some species of crop plants may be poor choices for introduction of resistance because they outcross with weedy species. Although the seed coating treatment will require that a resistance gene be expressed in the seed and possibly in the seedling and/or roots, it does not require that the resistance gene be expressed in the plant at other stages of development in other tissues, such as in leaves of juvenile or adult plants.

Promoters exist which would limit expression to the seed and/or seedling. These include promoters from genes which are expressed in the aleurone upon germination, such as the a-amylase gene Amy32b, from barley, (Whittier, R. F., Dean, D. A., and Rogers, J. C. 1987, Nucleic Acids Res. 6: 2515–2535); genes which are expressed in the developing embryo of the seed until very late in seed maturation, such as the globulin gene glb1, from maize (Belanger, F. C. and Kriz, A. L. 1991, Genetics 129: 863–872); and genes which are expressed both in the embryo during seed maturation and in the seedling during germination, such as the malate synthase gene MS-A from *Brassica napus* (Comai, L., Matsudaira, K. L., Heupel, R. C., Dietrich, R. A., and Harada, J. J. 1992, Plant Physiol. 98: 53–61), or the Em gene, from wheat, which is active in embryos of maturing seeds and ABA-inducible in seedlings. (Marcotte, W. R. Jr., Russell, S. H., and Quantrano, R. S. 1989, Plant Cell 1: 969–976).

A promoter active in the aleurone of germinating seeds would provide the expression needed to inactivate the chemical seed coating as it enters the seed. In the event that some chemical selective agent is able to penetrate the seed without being inactivated by the resistance gene product in the aleurone, a promoter expressed late in embryo development during seed maturation would provide a source of resistance gene product in the embryo prior to germination, so that no stunting of the embryo could occur by exposure to the selective agent before it could produce the resistance gene product. Expression of the resistance gene in germinating seedlings may be necessary to protect against residual selective agent in the soil, as well as any selective agent that is not inactivated by the resistance gene produce in the aleurone. Another option for protecting seedlings from any residual chemical selective agent in the soil would be a resistance gene driven by a root-specific promoter, such as the peroxidase gene POX1 from wheat (Hertig, C., Rebmann, G., Bull, Jr., Mauch, F., and Dudlet, R. 1991, Plant Molec. Biol. 16: 171–174).

While the strategy outlined above could be reasonably accomplished by a single pattern of expression or a combination of different patterns of expression of separate resistance transgenes, it is also possible that a single resistance transgene with a promoter or promoters conferring all of the necessary tissue specificities could be developed. This could be a promoter having one or more of the specificities described above, a combination of promoters with different patterns of expression, or a hybrid promoter derived from two or more promoters having different individual specificities as discussed above. Regardless of the particular approach, the seed coating system could be used on seed which germinate and survive, but produce plants which no longer express resistance beyond the seedling stage.

EXAMPLE 7

Use Of The NPT II Gene

Seed is obtained from several wild type and transgenic plants, for example corn, sorghum, soybeans, canola, sunflower, wheat, and other cereal or dicot plants, expressing the NPT II gene. The transgenic plants are identified based on enzyme or elisa assays for expression for the NPT II gene, PCR analysis of the structural gene for NPT II, and/or Southern analysis of NPT II. Individual transgenic and wild type plants are selfed to produce T0 seed for analysis. Typically, presence or absence of the NPT II gene is confirmed by PCR of seed chips of individual plants. Seeds are immersed in a combination of a Captan solution (10% active solution) and varying levels of kanamycin in aqueous solution ranging in concentration from 25 mg/l to 1000 mg/l with levels of 100 and 400 preferred. Both vacuum infiltration and simple coating of the seed are carried out with seed from each plant. Seed identified as NPT II positive and those identified as NPT II negative (wild type) are planted and subsequent germination attempted in a soil mix under greenhouse conditions.

A similar test can be performed in which wild type plant and transgenic plants known to express NPT II are pollinated with wild type plants. Seeds from each of the plants are coated as mentioned above and seed planted under greenhouse conditions. Wild type plants would be expected to show either no germination, or growth of albino plants. Seed from transgenic plants pollinated by wild type plants would be expected to segregation ratios consistent with a 1:1 ratio in which half germinate normally, and the other half either do not germinate or are albino. PCR analysis of the resultant green plants would be expected to be positive for the presence of the gene in all cases.

In another test, kanamycin is sprayed on seedlings with known identity at levels varying from 25 mg/l to 1000 mg/l. Those seedlings which contain the NPT II gene remain green while wild type plants demonstrate no germination or either an albino phenotype or loss of chlorophyll with the leaves present at the time of spraying.

The disclosures of all patents and other publications cited herein are hereby incorporated by reference. Although the foregoing invention has been described in detail for purposes of clarity of understanding, it will be apparent to those skilled in the art that certain modifications may be practiced within the scope of the appended claims.

What is claimed is:

1. A method for maintaining sterility in plants, the method comprising generating a transgenic parental plant line, the transgenic parental plant line comprising a sterility gene genetically linked to a resistance gene which confers resistance to a selective agent; increasing the transgenic parental plant line; coating seed of the increased transgenic parental plant line with a composition comprising the selective agent to which the resistance gene confers resistance; and producing sterile plants from the coated seed of the increased transgenic parental plant line.

2. The method of claim 1 wherein the sterility gene is selected from the group consisting of p.AN::Tox, dam methylase, or Barnase.

3. The method of claim 1 wherein the resistance gene confers resistance to a herbicide.

4. The method of claim 3 wherein the herbicide resistance gene confers resistance to a selective agent comprising a herbicide selected from the group consisting of amino acid synthesis inhibitors, photosynthesis inhibitors, lipid inhibitors, growth regulators, cell membrane disrupters, pigment inhibitors, and seedling growth inhibitors.

5. The method of claim 4 wherein the herbicide resistance gene confers resistance to a selective agent comprising a herbicide selected from the group consisting of imidazolinones, sulfonylureas, triazolopyrimidines, glyphosate, sethoxydim, fenoxaprop, glufosinate, the triazines, and bromoxynil.

6. The method of claim 3 wherein the herbicide resistance gene is selected from the group consisting of Bar, PAT, aroA, Epsps, Cor1-1, bxn, and psbA.

7. The method of claim 1 wherein the resistance gene confers resistance to an antibiotic.

8. The method of claim 7 wherein the antibiotic resistance gene confers resistance to a selective agent comprising an aminoglycoside antibiotic.

9. The method of claim 8 wherein the antibiotic resistance gene confers resistance to a selective agent comprising an aminoglycoside antibiotic selected from the group consisting of kanamycin, gentamycin, G418, neomycin, paromycin, and hygromycin.

10. The method of claim 7 wherein the antibiotic resistance gene is selected from the group consisting of the NPT II gene, the aphA2 gene, and the hpt-aphlV gene.

11. The method of claim 1 wherein the resistance gene confers resistance to a selective agent comprising a toxic chemical other than an herbicide or an antibiotic.

12. The method of claim 11 wherein the toxic chemical comprises a toxic metabolite.

13. The method of claim 12 wherein the toxic metabolite is 4-methyltryptohan.

14. The method of claim 11 wherein the resistance gene is the tryptophan decarboxylase gene.

15. The method of claim 1 wherein the transgenic parental plant line further comprises a constitutive promoter linked to the resistance gene.

16. The method of claim 15 wherein the constitutive promoter is selected from the group comprising CaMV 19S, CaMV 35S, CaMV double 35S, ALS, MAS, and ubiquitin.

17. The method of claim 1 wherein the transgenic parental plant line further comprises a chemically inducible gene that controls expression of the resistance gene.

18. The method of claim 17 wherein the chemically inducible gene is induced by a hormone.

19. The method of claim 18 wherein the hormone is asteroid hormone.

20. The method of claim 17 where the chemically inducible gene is induced by a non-hormone chemical.

21. The method of claim 20 wherein the non-hormone chemical is a safener.

22. The method of claim 1 wherein the transgenic parental plant line further comprises at least one tissue-specific promoter.

23. The method of claim 22 wherein the tissue-specific promoter is a seed-specific promoter.

24. The method of claim 17 wherein the seed of increased transgenic parental plant line is coated with a composition which further comprises an effective amount of the chemical which induces the chemically inducible gene.

25. The method of claim 24 wherein the chemical which induces the chemically inducible gene is selected from the group consisting of hormones and safeners.

26. Mature plants produced by the method of claim 1.

27. Plant seed produced by the mature plants of claim 26.

28. A method for maintaining male sterility in plants, the method comprising generating a transgenic parental plant line, the transgenic parental plant line comprising a male sterility gene genetically linked to a resistance gene which confers resistance to a selective agent, the resistance gene being under the control of a chemically inducible gene; increasing the transgenic parental plant line; coating seed of the increased transgenic parental plant line with a composition comprising effective amounts of the selective agent to which the resistance gene confers resistance and of the chemical to which the chemically inducible gene is responsive; and producing male sterile plants from the coated seed of the increased transgenic parental plant line.

29. A method for maintaining male sterility in plants, the method comprising generating a transgenic parental plant line, the transgenic parental plant line comprising a male sterility gene genetically linked to a resistance gene which confers resistance to a selective agent, the resistance gene being under the control of a seed specific promoter; increasing the transgenic parental plant line; coating seed of the increased transgenic parental plant line with a composition comprising an effective amount of the selective agent to which the resistance gene confers resistance; and producing male sterile plants from the coated seed of the increased transgenic, parental plant line.

* * * * *